(12) United States Patent
Adawi et al.

(10) Patent No.: US 12,161,400 B2
(45) Date of Patent: *Dec. 10, 2024

(54) IDENTIFYING PULMONARY VEIN OCCLUSION BY DIMENSION DEFORMATIONS OF BALLOON CATHETER

(71) Applicant: Biosense Webster (Israel) Ltd., Yokneam (IL)

(72) Inventors: Eid Adawi, Tur'an (IL); Zvi Dekel, Zichron Yaakov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/304,537

(22) Filed: Apr. 21, 2023

(65) Prior Publication Data
US 2023/0248429 A1 Aug. 10, 2023

Related U.S. Application Data

(63) Continuation of application No. 16/593,246, filed on Oct. 4, 2019, now Pat. No. 11,633,228.

(51) Int. Cl.
*A61B 5/00* (2006.01)
*A61B 5/06* (2006.01)
(Continued)

(52) U.S. Cl.
CPC .......... *A61B 18/1492* (2013.01); *A61B 5/065* (2013.01); *A61B 5/6853* (2013.01);
(Continued)

(58) Field of Classification Search
None
See application file for complete search history.

(56) References Cited

U.S. PATENT DOCUMENTS

D123,782 S 12/1940 Paul
3,316,896 A 5/1967 Louis
(Continued)

FOREIGN PATENT DOCUMENTS

CN 101422637 A 5/2009
CN 102271607 A 12/2011
(Continued)

OTHER PUBLICATIONS

Extended European Search Report issued in European Patent Application No. 20199789.7.
(Continued)

*Primary Examiner* — Michael F Peffley
*Assistant Examiner* — Nicholas S Borsch
(74) *Attorney, Agent, or Firm* — Troutman Pepper Hamilton Sanders LLP (57) ABSTRACT

A method includes receiving position signals that are indicative of positions of multiple electrodes disposed on an expandable balloon that is fitted at a distal end of a shaft for engaging a lumen of an organ to occlude the lumen. Based on the received position signals, a change is calculated in one or more dimensions of the balloon between (i) a first configuration in which the balloon is inflated but not engaged in the lumen, and (ii) a second configuration in which the balloon is inflated and engaged in the lumen. Using the calculated change, a degree is estimated to which the balloon occludes the lumen. The estimated degree of occlusion is presented to a user.

20 Claims, 3 Drawing Sheets

(51) Int. Cl.
 *A61B 18/00* (2006.01)
 *A61B 18/14* (2006.01)
(52) U.S. Cl.
 CPC ............... *A61B 2018/0022* (2013.01); *A61B 2018/00577* (2013.01)

(56) References Cited

U.S. PATENT DOCUMENTS

| | | | |
|---|---|---|---|
| 4,276,874 A | 7/1981 | Wolvek et al. | |
| 4,587,975 A | 5/1986 | Salo et al. | |
| 4,709,698 A | 12/1987 | Johnston et al. | |
| 4,805,621 A | 2/1989 | Heinze et al. | |
| 5,178,957 A | 1/1993 | Kolpe et al. | |
| 5,391,199 A | 2/1995 | Ben-Haim | |
| 5,429,617 A | 7/1995 | Hammersmark et al. | |
| 5,582,609 A | 12/1996 | Swanson et al. | |
| 5,584,830 A | 12/1996 | Ladd et al. | |
| 5,702,386 A | 12/1997 | Stern et al. | |
| 5,718,241 A | 2/1998 | Ben-Haim et al. | |
| 5,795,325 A | 4/1998 | Valley et al. | |
| 5,797,903 A | 8/1998 | Swanson et al. | |
| 5,860,974 A | 1/1999 | Abele | |
| 5,971,983 A | 10/1999 | Lesh | |
| 6,012,457 A | 1/2000 | Lesh | |
| 6,024,740 A | 2/2000 | Lesh et al. | |
| 6,042,580 A | 3/2000 | Simpson | |
| 6,123,718 A | 9/2000 | Tu et al. | |
| 6,164,283 A | 12/2000 | Lesh | |
| 6,171,275 B1 | 1/2001 | Webster, Jr. | |
| 6,176,832 B1 | 1/2001 | Habu et al. | |
| 6,198,974 B1 | 3/2001 | Webster, Jr. | |
| 6,226,542 B1 | 5/2001 | Reisfeld | |
| 6,239,724 B1 | 5/2001 | Doron et al. | |
| 6,301,496 B1 | 10/2001 | Reisfeld | |
| 6,322,558 B1 | 11/2001 | Taylor et al. | |
| 6,332,089 B1 | 12/2001 | Acker et al. | |
| 6,380,957 B1 | 4/2002 | Banning | |
| 6,402,740 B1 | 6/2002 | Ellis et al. | |
| D462,389 S | 9/2002 | Provence et al. | |
| 6,471,693 B1 | 10/2002 | Carroll et al. | |
| 6,484,118 B1 | 11/2002 | Govari | |
| 6,522,930 B1 | 2/2003 | Schaer et al. | |
| 6,618,612 B1 | 9/2003 | Acker et al. | |
| 6,656,174 B1 | 12/2003 | Hegde et al. | |
| 6,690,963 B2 | 2/2004 | Ben-Haim et al. | |
| 6,814,733 B2 | 11/2004 | Schwartz et al. | |
| 6,893,433 B2 | 5/2005 | Lentz | |
| 6,986,744 B1 | 1/2006 | Krivitski | |
| 6,987,995 B2 | 1/2006 | Drysen | |
| 6,997,924 B2 | 2/2006 | Schwartz et al. | |
| 7,142,903 B2 | 11/2006 | Rodriguez et al. | |
| 7,156,816 B2 | 1/2007 | Schwartz et al. | |
| 7,274,957 B2 | 9/2007 | Drysen | |
| 7,340,307 B2 | 3/2008 | Maguire et al. | |
| 7,377,906 B2 | 5/2008 | Selkee | |
| 7,442,190 B2 | 10/2008 | Abbound et al. | |
| 7,536,218 B2 | 5/2009 | Govari et al. | |
| 7,591,799 B2 | 9/2009 | Selkee | |
| 7,593,760 B2 | 9/2009 | Rodriguez et al. | |
| 7,720,517 B2 | 5/2010 | Drysen | |
| 7,756,576 B2 | 7/2010 | Levin | |
| 7,842,031 B2 | 11/2010 | Abboud et al. | |
| 7,848,787 B2 | 12/2010 | Osadchy | |
| 7,853,302 B2 | 12/2010 | Rodriguez et al. | |
| 7,869,865 B2 | 1/2011 | Govari et al. | |
| 8,000,765 B2 | 8/2011 | Rodriguez et al. | |
| 8,021,327 B2 | 9/2011 | Selkee | |
| 8,048,032 B2 | 11/2011 | Root et al. | |
| 8,231,617 B2 | 7/2012 | Satake | |
| 8,267,932 B2 | 9/2012 | Baxter et al. | |
| 8,275,440 B2 | 9/2012 | Rodriguez et al. | |
| 8,348,888 B2 | 1/2013 | Selkee | |
| 8,357,152 B2 | 1/2013 | Govari et al. | |
| D682,289 S | 5/2013 | DiJulio et al. | |
| D682,291 S | 5/2013 | Baek et al. | |
| 8,456,182 B2 | 6/2013 | Bar-Tal et al. | |
| D690,318 S | 9/2013 | Kluttz et al. | |
| D694,652 S | 12/2013 | Tompkin | |
| 8,641,709 B2 | 2/2014 | Sauvageau et al. | |
| 8,721,590 B2 | 5/2014 | Seward et al. | |
| 8,777,161 B2 | 7/2014 | Pollock et al. | |
| D716,340 S | 10/2014 | Bresin et al. | |
| 8,852,181 B2 | 10/2014 | Malecki et al. | |
| D720,766 S | 1/2015 | Mandal et al. | |
| D721,379 S | 1/2015 | Moon et al. | |
| D724,618 S | 3/2015 | Shin | |
| 8,998,893 B2 | 4/2015 | Avitall | |
| D729,263 S | 5/2015 | Ahn et al. | |
| 9,089,350 B2 | 7/2015 | Willard | |
| D736,780 S | 8/2015 | Wang | |
| 9,126,023 B1 | 9/2015 | Sahatjian et al. | |
| D740,308 S | 10/2015 | Kim et al. | |
| D743,424 S | 11/2015 | Danielyan et al. | |
| D744,000 S | 11/2015 | Villamor et al. | |
| 9,173,758 B2 | 11/2015 | Brister et al. | |
| D747,742 S | 1/2016 | Fan et al. | |
| D750,644 S | 3/2016 | Bhutani et al. | |
| 9,283,034 B2 | 3/2016 | Katoh et al. | |
| 9,289,141 B2 | 3/2016 | Lowery et al. | |
| D753,690 S | 4/2016 | Vazquez et al. | |
| 9,320,631 B2 | 4/2016 | Moore et al. | |
| 9,345,540 B2 | 5/2016 | Mallin et al. | |
| D759,673 S | 6/2016 | Looney et al. | |
| D759,675 S | 6/2016 | Looney et al. | |
| D764,500 S | 8/2016 | Wang | |
| D765,709 S | 9/2016 | Gagnier | |
| D767,616 S | 9/2016 | Jones et al. | |
| D768,696 S | 10/2016 | Gagnier | |
| D783,037 S | 4/2017 | Hariharan et al. | |
| 9,636,172 B2 | 5/2017 | Hu | |
| 9,655,677 B2 | 5/2017 | Salahieh et al. | |
| D791,805 S | 7/2017 | Segars | |
| 9,795,442 B2 | 10/2017 | Salahieh et al. | |
| 9,907,610 B2 | 3/2018 | Beeckler et al. | |
| 9,956,035 B2 | 5/2018 | Govari et al. | |
| D861,717 S | 10/2019 | Brekke et al. | |
| 10,688,278 B2 | 6/2020 | Beeckler et al. | |
| 11,633,228 B2 * | 4/2023 | Adawi ............. A61B 5/065 604/509 |
| 2001/0031961 A1 | 10/2001 | Hooven | |
| 2002/0002369 A1 | 1/2002 | Hood | |
| 2002/0065455 A1 | 5/2002 | Ben-Haim et al. | |
| 2002/0068931 A1 | 6/2002 | Wong et al. | |
| 2002/0077627 A1 | 6/2002 | Johnson et al. | |
| 2002/0160134 A1 | 10/2002 | Ogushi et al. | |
| 2003/0018327 A1 | 1/2003 | Truckai et al. | |
| 2003/0028183 A1 | 2/2003 | Sanchez et al. | |
| 2003/0050637 A1 | 3/2003 | Maguire et al. | |
| 2003/0060820 A1 | 3/2003 | Maguire et al. | |
| 2003/0120150 A1 | 6/2003 | Govari | |
| 2003/0144658 A1 | 7/2003 | Schwartz et al. | |
| 2003/0199923 A1 | 10/2003 | Khairkhahan et al. | |
| 2004/0068178 A1 | 4/2004 | Govari | |
| 2004/0122445 A1 | 6/2004 | Butler et al. | |
| 2004/0147920 A1 | 7/2004 | Keidar | |
| 2004/0225285 A1 | 11/2004 | Gibson | |
| 2005/0070887 A1 | 3/2005 | Taimisto et al. | |
| 2005/0119686 A1 | 6/2005 | Clubb | |
| 2006/0013595 A1 | 1/2006 | Trezza et al. | |
| 2006/0106375 A1 | 5/2006 | Werneth et al. | |
| 2006/0135953 A1 | 6/2006 | Kania et al. | |
| 2007/0071792 A1 | 3/2007 | Varner et al. | |
| 2007/0080322 A1 | 4/2007 | Walba | |
| 2007/0083194 A1 | 4/2007 | Kunis et al. | |
| 2007/0287994 A1 | 12/2007 | Patel | |
| 2008/0018891 A1 | 1/2008 | Hell et al. | |
| 2008/0021313 A1 | 1/2008 | Eidenschink et al. | |
| 2008/0051707 A1 | 2/2008 | Phan et al. | |
| 2008/0140072 A1 | 6/2008 | Stangenes et al. | |
| 2008/0183132 A1 | 7/2008 | Davies et al. | |
| 2008/0188912 A1 | 8/2008 | Stone et al. | |
| 2008/0202637 A1 | 8/2008 | Hector et al. | |
| 2008/0208186 A1 | 8/2008 | Slater | |
| 2008/0249463 A1 | 10/2008 | Pappone et al. | |

(56) References Cited

U.S. PATENT DOCUMENTS

| | | |
|---|---|---|
| 2008/0262489 A1 | 10/2008 | Steinke |
| 2008/0281312 A1 | 11/2008 | Werneth et al. |
| 2009/0163890 A1 | 6/2009 | Clifford et al. |
| 2009/0182318 A1 | 7/2009 | Abboud et al. |
| 2009/0270850 A1 | 10/2009 | Zhou et al. |
| 2009/0326526 A1* | 12/2009 | Ingle ............... A61B 18/0218 |
| | | 606/21 |
| 2010/0069836 A1 | 3/2010 | Satake |
| 2010/0094328 A1 | 4/2010 | O'dea et al. |
| 2010/0114269 A1 | 5/2010 | Wittenberger et al. |
| 2010/0204560 A1 | 8/2010 | Salahieh et al. |
| 2010/0256629 A1 | 10/2010 | Wylie et al. |
| 2010/0324552 A1 | 12/2010 | Kauphusman et al. |
| 2011/0118632 A1 | 5/2011 | Sinelnikov et al. |
| 2011/0130648 A1 | 6/2011 | Beeckler et al. |
| 2011/0184400 A1 | 7/2011 | Pageard |
| 2011/0282338 A1 | 11/2011 | Fojtik |
| 2011/0295248 A1 | 12/2011 | Wallace et al. |
| 2011/0301587 A1 | 12/2011 | Deem et al. |
| 2011/0313286 A1 | 12/2011 | Whayne et al. |
| 2012/0019107 A1 | 1/2012 | Gabl et al. |
| 2012/0029511 A1 | 2/2012 | Smith et al. |
| 2012/0065503 A1 | 3/2012 | Rogers et al. |
| 2012/0071870 A1 | 3/2012 | Salahieh et al. |
| 2012/0079427 A1 | 3/2012 | Carmichael et al. |
| 2012/0101413 A1 | 4/2012 | Beetel et al. |
| 2012/0101538 A1 | 4/2012 | Ballakur et al. |
| 2012/0143177 A1 | 6/2012 | Avitall |
| 2012/0143179 A1 | 6/2012 | Avitall |
| 2012/0143293 A1 | 6/2012 | Mauch et al. |
| 2012/0191079 A1 | 7/2012 | Moll et al. |
| 2012/0209260 A1 | 8/2012 | Lambert et al. |
| 2013/0085360 A1 | 4/2013 | Grunewald |
| 2013/0090649 A1 | 4/2013 | Smith et al. |
| 2013/0109982 A1 | 5/2013 | Sato et al. |
| 2013/0116550 A1 | 5/2013 | Ishii et al. |
| 2013/0150693 A1 | 6/2013 | D'Angelo et al. |
| 2013/0165916 A1 | 6/2013 | Mathur et al. |
| 2013/0165941 A1 | 6/2013 | Murphy |
| 2013/0165990 A1 | 6/2013 | Mathur et al. |
| 2013/0169624 A1 | 7/2013 | Bourier et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0282084 A1 | 10/2013 | Mathur et al. |
| 2013/0318439 A1 | 11/2013 | Landis et al. |
| 2014/0012242 A1 | 1/2014 | Lee et al. |
| 2014/0018788 A1 | 1/2014 | Engelman et al. |
| 2014/0031813 A1 | 1/2014 | Tellio et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0227437 A1 | 8/2014 | DeBoer et al. |
| 2014/0243821 A1 | 8/2014 | Salahieh et al. |
| 2014/0275993 A1 | 9/2014 | Ballakur |
| 2014/0276756 A1 | 9/2014 | Hill |
| 2014/0276811 A1 | 9/2014 | Koblish et al. |
| 2014/0288546 A1 | 9/2014 | Sherman et al. |
| 2014/0330262 A1 | 11/2014 | Jannicke et al. |
| 2014/0330266 A1 | 11/2014 | Thompson et al. |
| 2014/0357956 A1 | 12/2014 | Salahieh et al. |
| 2014/0358137 A1 | 12/2014 | Hu |
| 2015/0005799 A1 | 1/2015 | Lindquist et al. |
| 2015/0025532 A1 | 1/2015 | Hanson et al. |
| 2015/0025533 A1 | 1/2015 | Groff et al. |
| 2015/0057655 A1 | 2/2015 | Osypka |
| 2015/0067512 A1 | 3/2015 | Roswell |
| 2015/0080883 A1 | 3/2015 | Haverkost et al. |
| 2015/0105774 A1 | 4/2015 | Lindquist et al. |
| 2015/0112256 A1 | 4/2015 | Byrne et al. |
| 2015/0112321 A1 | 4/2015 | Cadouri |
| 2015/0119875 A1 | 4/2015 | Fischell et al. |
| 2015/0141982 A1 | 5/2015 | Lee |
| 2015/0157382 A1 | 6/2015 | Avitall et al. |
| 2015/0164570 A1 | 6/2015 | Wittenberger et al. |
| 2015/0216591 A1 | 8/2015 | Cao et al. |
| 2015/0216650 A1 | 8/2015 | Shaltis |
| 2015/0223704 A1 | 8/2015 | Haverkost et al. |
| 2015/0223729 A1* | 8/2015 | Balachandran ...... A61B 5/1076 |
| | | 600/374 |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0272667 A1 | 10/2015 | Govari et al. |
| 2015/0327805 A1 | 11/2015 | Ben-Haim |
| 2015/0341752 A1 | 11/2015 | Flynn |
| 2016/0000499 A1 | 1/2016 | Lennox et al. |
| 2016/0051321 A1 | 2/2016 | Salahieh et al. |
| 2016/0085431 A1 | 3/2016 | Kim et al. |
| 2016/0106499 A1 | 4/2016 | Ogata et al. |
| 2016/0166306 A1 | 6/2016 | Pageard |
| 2016/0175041 A1 | 6/2016 | Govari et al. |
| 2016/0196635 A1 | 7/2016 | Cho et al. |
| 2016/0256305 A1 | 9/2016 | Longo et al. |
| 2016/0374748 A9 | 12/2016 | Salahieh et al. |
| 2017/0042614 A1 | 2/2017 | Salahieh et al. |
| 2017/0042615 A1 | 2/2017 | Salahieh et al. |
| 2017/0080192 A1 | 3/2017 | Giasolli et al. |
| 2017/0143359 A1 | 5/2017 | Nguyen et al. |
| 2017/0164464 A1 | 6/2017 | Weinkam et al. |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0333122 A1 | 11/2017 | Rajagopalan et al. |
| 2017/0347896 A1 | 12/2017 | Keyes et al. |
| 2018/0074693 A1 | 3/2018 | Jones et al. |
| 2018/0076366 A1 | 3/2018 | Halbritter et al. |
| 2018/0110562 A1 | 4/2018 | Govari et al. |
| 2018/0125575 A1 | 5/2018 | Schwartz et al. |
| 2018/0256247 A1 | 9/2018 | Govari et al. |
| 2018/0280080 A1 | 10/2018 | Govari et al. |
| 2018/0333162 A1 | 11/2018 | Saab |
| 2018/0368927 A1 | 12/2018 | Lyons et al. |
| 2019/0059818 A1 | 2/2019 | Herrera et al. |
| 2019/0060622 A1 | 2/2019 | Beeckler |
| 2019/0143079 A1 | 5/2019 | Beeckler et al. |
| 2019/0175262 A1 | 6/2019 | Govari et al. |
| 2019/0175263 A1 | 6/2019 | Altmann et al. |
| 2019/0175264 A1 | 6/2019 | Govari et al. |
| 2019/0183567 A1 | 6/2019 | Govari et al. |
| 2019/0201669 A1 | 7/2019 | Govari et al. |
| 2019/0217065 A1 | 7/2019 | Govari et al. |
| 2019/0297441 A1 | 9/2019 | Dehe et al. |
| 2019/0298441 A1 | 10/2019 | Clark et al. |
| 2019/0350489 A1 | 11/2019 | Ludwin et al. |
| 2019/0365451 A1 | 12/2019 | Jung, Jr. |
| 2020/0001054 A1 | 1/2020 | Jimenez et al. |
| 2020/0015693 A1 | 1/2020 | Beeckler et al. |
| 2020/0085497 A1 | 3/2020 | Zhang et al. |
| 2020/0155226 A1 | 5/2020 | Valls et al. |
| 2021/0169567 A1 | 6/2021 | Govari et al. |

FOREIGN PATENT DOCUMENTS

| | | |
|---|---|---|
| CN | 102458566 A | 5/2012 |
| CN | 203539434 U | 4/2014 |
| CN | 104244856 A | 12/2014 |
| CN | 104546117 A | 4/2015 |
| CN | 105105844 A | 12/2015 |
| CN | 105473091 A | 4/2016 |
| CN | 105473093 A | 4/2016 |
| EP | 0779059 A1 | 6/1997 |
| EP | 1790304 A2 | 5/2007 |
| EP | 2749214 A1 | 7/2014 |
| EP | 2865350 A2 | 4/2015 |
| EP | 2875790 A2 | 5/2015 |
| EP | 3238646 A2 | 11/2017 |
| EP | 3238648 A1 | 11/2017 |
| EP | 3251622 A1 | 12/2017 |
| EP | 3300680 A1 | 4/2018 |
| EP | 3315087 A1 | 5/2018 |
| EP | 3332727 A2 | 6/2018 |
| EP | 3571983 A2 | 11/2019 |
| EP | 3586778 A1 | 1/2020 |

(56) References Cited

FOREIGN PATENT DOCUMENTS

| | | |
|---|---|---|
| EP | 3653153 A1 | 5/2020 |
| JP | H06261951 A | 9/1994 |
| JP | H1176233 A | 3/1999 |
| JP | 2000504242 A | 4/2000 |
| JP | 2005052424 A | 3/2005 |
| JP | 2010507404 A | 3/2010 |
| JP | 2011526190 A | 10/2011 |
| JP | 2012024156 A | 2/2012 |
| JP | 2013013726 A | 1/2013 |
| JP | 2013078587 A | 5/2013 |
| JP | 2013529109 A | 7/2013 |
| JP | 2014529419 A | 11/2014 |
| JP | 2015503365 A | 2/2015 |
| JP | 2015100706 A | 6/2015 |
| JP | 2015112113 A | 6/2015 |
| JP | 2015112114 A | 6/2015 |
| JP | 2015518776 A | 7/2015 |
| JP | 2016515442 A | 5/2016 |
| JP | 2016116863 A | 6/2016 |
| JP | 2017217473 A | 12/2017 |
| JP | 2019103808 A | 6/2019 |
| WO | 96/05768 A1 | 2/1996 |
| WO | 0056237 A2 | 9/2000 |
| WO | 02102231 A2 | 12/2002 |
| WO | 2005041748 A2 | 5/2005 |
| WO | 2008049087 A2 | 4/2008 |
| WO | 2011143468 A2 | 11/2011 |
| WO | 2013022853 A1 | 2/2013 |
| WO | 2013049601 A2 | 4/2013 |
| WO | 2013052919 A2 | 4/2013 |
| WO | 2013154776 A2 | 10/2013 |
| WO | 2014168987 A1 | 10/2014 |
| WO | 2015049784 A1 | 4/2015 |
| WO | 2016183337 A2 | 11/2016 |
| WO | 2016210437 A1 | 12/2016 |
| WO | 2017024306 A1 | 2/2017 |
| WO | 2017087549 A1 | 5/2017 |
| WO | 2018106569 A1 | 6/2018 |
| WO | 2018129133 A1 | 7/2018 |
| WO | 2019095020 A1 | 5/2019 |

OTHER PUBLICATIONS

Angela O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages, [Retrieved on Dec. 16, 2020] Retrieved from URL: https://cardiacrhythmnews.com/fist-in-man-study-shows-promising-results-with-a-multi-electrode-radiofrequency-balloon-for-paroxysmal-af-treatment/.

Casella M., et al., "Ablation Index as a Predictor of Long-Term Efficacy in Premature Ventricular Complex Ablation: A Regional Target Value Analysis," Heart Rhythm Society, Jun. 2019, vol. 16, No. 6, pp. 888-895.

Co-Pending U.S. Appl. No. 14/578,807, filed Dec. 22, 2014, 21 pages.

Das M., et al., "Ablation Index, a Novel Marker of Ablation Lesion Quality: Prediction of Pulmonary Vein Reconnection at Repeat Electrophysiology Study and Regional Differences in Target Values," Europace, 2017, Published Online May 31, 2016, vol. 19, pp. 775-783.

Dorobantu M., et al., "Oral Anticoagulation During Atrial Fibrillation Ablation: Facts and Controversies," Cor et Vasa, 2013, Accepted on Dec. 3, 2012, vol. 55, No. 2, pp. e101-e106, Retrieved from URL: https://www.sciencedirect.com/science/article/pii/S0010865012001415.

Extended European Search Report for Application No. EP17168513.4 mailed Sep. 18, 2017, 11 pages.

Extended European Search Report for European Application No. 15201723.2, mailed May 11, 2016, 07 Pages.

Extended European Search Report for European Application No. 17168393.1 mailed Dec. 15, 2017, 12 Pages.

Extended European Search Report for European Application No. 17168518.3, mailed Sep. 20, 2017, 9 Pages.

Extended European Search Report for European Application No. 17173893.3, mailed Nov. 6, 2017, 8 Pages.

Extended European Search Report for European Application No. 17201434.2, mailed Feb. 1, 2018, 10 Pages.

Extended European Search Report for European Application No. 17205876.0, mailed Jun. 1, 2018, 13 Pages.

Extended European Search Report for European Application No. 19177365.4, mailed Nov. 8, 2019, 07 Pages.

Extended European Search Report for European Application No. 19183327.6, mailed Nov. 21, 2019, 8 Pages.

Extended European Search Report for European Application No. 20153872.5, mailed May 7, 2020, 9 Pages.

Extended European Search Report for European Application No. 20195648.9, mailed Feb. 12, 2021, 8 Pages.

Fornell D., "Multi-Electrode RF Balloon Efficient for Acute Pulmonary Vein Isolation," Diagnostic and Interventional Cardiology, May 17, 2017, 3 Pages, [Retrieved on Dec. 16, 2020] Retrieved from URL: www.dicardiology.com/article/multi-electrode-rf-balloon-efficient-acute-pulmonary-vein-isolation.

Haines D.E., et al., "The Promise of Pulsed Field Ablation," Dec. 2019, vol. 19, No. 12, 10 pages.

Honarbakhsh S., et al., "Radiofrequency Balloon Catheter Ablation for Paroxysmal Atrial Fibrillation, Radiance Study—a UK experience," EP Europace, Oct. 2017, vol. 19, No. 1, p. i21, 3 Pages.

Nagashima K., et al., "Hot Balloon Versus Cryoballoon Ablation for Atrial Fibrillation," Circulation: Arrhythmia and Electrophysiology, May 2018, vol. 11, No. 5, e005861, 9 Pages.

Napoli N., et al., "For Atrial Fibrillation Ablation, Newer Anticoagulant Reduces Major Bleeds," American College of Cardiology, Mar. 19, 2017, 4 Pages, [Retrieved on Jan. 21, 2022] Retrieved from URL: https://www.acc.org/about-acc/press-releases/2017/03/18/08/47/sun-1045am-for-atrial-fibrillation-ablation-newer-anticoagulant-reduces-major-bleeds.

Okano T., et al., "Wire Perforation Causing Cardiopulmonary Arrest During Radiofrequency Hot Balloon Ablation for Pulmonary Vein Isolation," Journal of Cardiology Cases, Feb. 15, 2019, vol. 19, No. 5, pp. 169-172.

Partial European Search Report for European Application No. 17168393.1 mailed Sep. 13, 2017, 13 Pages.

Partial European Search Report for European Application No. 17205876.0, mailed Feb. 22, 2018, 10 Pages.

Reddy V.Y., et al., "Balloon Catheter Ablation to Treat Paroxysmal Atrial Fibrillation: What is the Level of Pulmonary Venous Isolation?," Heart Rhythm, Mar. 2008, vol. 5, No. 3, pp. 353-360, 3 Pages.

Winkle R.A., et al., "Atrial Fibrillation Ablation Using Open-Irrigated Tip Radiofrequency: Experience with Intraprocedural Activated Clotting Times ≤ 210 Seconds," Heart Rhythm, Jun. 2014, Epub Mar. 27, 2014, vol. 11, No. 6, pp. 963-968.

Youtube:, "Intensity™ CX4 Professional E-Stim/ Ultrasound Combo," Dec. 22, 2015, 1 Page, [Retrieved on Nov. 19, 2020], Retrieved from URL: https://www.youtube.com/watch?v=76s1QkMWJME].

Youtube: "New Interface TactiCath Contact Force Ablation Catheter," Nov. 26, 2013, 1 Pages, [Retrieved on Nov. 19, 2020], Retrieved from URL: https: /Awww.youtube.com/watch?v=aYvYO8Hpylg].

Search Reported dated Oct. 31, 2023, from corresponding European Application No. 20199789.7.

English translation of Search Report dated Mar. 26, 2024, from corresponding Japanese Application No. 2020-167546.

English translation of Notice of Reasons for Refusal dated Apr. 9, 2024, from corresponding Japanese Application No. 2020-167546.

English translation of Written Opinion dated Jun. 28, 2024, from corresponding Japanese Application No. 2020-167546.

* cited by examiner

IDENTIFYING PULMONARY VEIN OCCLUSION BY DIMENSION DEFORMATIONS OF BALLOON CATHETER

CROSS-REFERENCE TO RELATED APPLICATIONS

This application is a continuation application under U.S.C. § 120 of U.S. patent application Ser. No. 16/593,246 filed Oct. 4, 2019, the entire contents of which are incorporated herein by reference.

FIELD OF THE INVENTION

The present invention relates generally to tracking a medical probe inside a living body, and specifically to tracking a shape of the medical probe.

BACKGROUND OF THE INVENTION

Expandable probes for occluding a lumen in the body were previously proposed in the patent literature. For example, U.S. Pat. No. 5,795,325 describes measurement of pressure on both sides of an occluding balloon for determining when pressure forces on the balloon may cause migration of the balloon. An alarm indicates when the pressure force on the balloon exceed a predetermined threshold. In another aspect of the invention, a pressure monitor determines when a rate of pressure increase with respect to the fluid volume in the balloon reaches a predetermined threshold when inflating the occluding balloon. A predetermined amount of fluid is then added to the balloon so that the balloon is not under-inflated or over-inflated.

As another example, U.S. Patent Application Publication 2011/0184400 describes a method and system for cryogenically ablating large areas of tissue within the left atrium. In an exemplary embodiment, a cryotherapy device includes a catheter body, a proximal end and a distal end, a first lumen, a second lumen, and an ablation element expandable from a first diameter to a second diameter. The ablation element has a surface portion that conforms to the uneven surface topography of the cardiac tissue. The ablation element can include one or more deformable balloons and/or flexible elements. The surface of the balloon can further be shaped by regulation of pressure within the one or more balloons. Further, as there may be variations in the size, shape or other dimensions of the vessel being occluded, a second balloon may be selectively, controllably expanded to a fraction of its overall inflation/size capacity to obtain the resulting, desired occlusion. In an exemplary method, a tissue ablation device is provided and tissue in the left atrium is ablated with the device, whereby the ablation is created by freezing tissue.

SUMMARY OF THE INVENTION

An embodiment of the present invention provides a method including receiving position signals that are indicative of positions of multiple electrodes disposed on an expandable balloon that is fitted at a distal end of a shaft for engaging a lumen of an organ to occlude the lumen. Based on the received position signals, a change is calculated in one or more dimensions of the balloon between (i) a first configuration in which the balloon is inflated but not engaged in the lumen, and (ii) a second configuration in which the balloon is inflated and engaged in the lumen. Using the calculated change, a degree is estimated to which the balloon occludes the lumen. The estimated degree of occlusion is presented to a user.

In some embodiments, estimating the degree includes deriving a Balloon Inflation Index (BII) from the calculated change in the dimensions, and estimating the degree to which the balloon occludes the lumen based on the BII.

In some embodiments, calculating the change in dimensions includes calculating a change in a radius of the balloon.

In an embodiment, calculating the change in the radius of the balloon includes:

measuring positions of ablation electrodes disposed over the expandable balloon using Active Current Location (ACL). A circle is best fitted to the measured positions. A radius of the best fitted circle is calculated.

In another embodiment, receiving the position signals includes receiving additional position signals from one or more position sensors disposed on the distal end of the shaft, and wherein calculating the change in dimensions includes calculating a change in a length of the balloon along a longitudinal axis of the balloon based on the additional position signals.

In some embodiments, estimating the degree to which the balloon occludes the lumen includes numerically grading the degree. In other embodiments, estimating the degree to which the balloon occludes the lumen includes textually grading the degree.

In an embodiment, the lumen includes an ostium of a pulmonary vein (PV).

There is additionally provided, in accordance with an embodiment of the present invention, a system including an interface and a processor. The interface is configured to receive position signals that are indicative of positions of multiple electrodes disposed on an expandable balloon that is fitted at a distal end of a shaft for engaging a lumen of an organ to occlude the lumen. The processor is configured to (a) based on the received position signals, calculate a change in one or more dimensions of the balloon, (b) using the calculated change in dimensions, estimate a degree to which the balloon occludes the lumen, and (c) present the estimated degree of occlusion to a user.

The present invention will be more fully understood from the following detailed description of the embodiments thereof, taken together with the drawings in which:

DETAILED DESCRIPTION OF EMBODIMENTS

Overview

For efficient ablation of tissue of a lumen using a balloon catheter, such as a radiofrequency (RF) ablation balloon catheter, it is important that the ablating electrodes disposed over the balloon membrane are in good physical contact with the tissue being ablated. For example, for a safe and effective pulmonary vein (PV) isolation, all ablation electrodes should be in good contact over a perimeter of a circularly shaped ostium of the PV. Therefore, it is important, before performing the ablation, to ensure that the balloon fully occludes the vein.

However, checking for full occlusion of a lumen, such as of a circular ostium, for example, by checking for occlusion of a distal blood vessel (e.g., of the PV), is a process that conventionally relies on another modality, such as fluoroscopy. Unfortunately, fluoroscopy (i.e., observing the behavior of an X-ray opaque contrast agent after it has been injected) may sometimes have side effects related to the contrast material itself and to the use of X-ray radiation.

Embodiments of the present invention that are described hereinafter provide improved techniques for monitoring, e.g., immediately before ablation, how well an expandable (e.g., inflatable) cardiac ablation balloon occludes a circular lumen, such as an ostium of a PV. The disclosed techniques provide systems and methods that can provide a physician with an estimated degree of occlusion by estimating a degree to which the balloon occludes the lumen. To derive the estimation, a processor calculates a change in one or more dimensions of the balloon between (i) a first configuration in which the balloon is inflated but not engaged in the lumen, and (ii) a second configuration in which the balloon is inflated and engaged in the lumen.

In some embodiments, the estimation of balloon occlusion relies on an estimated degree of balloon inflation while the balloon is pressed against a wall of a circular lumen, using a balloon inflation index (BII).

In some embodiments, a processor (e.g., a processor of the ablation system) derives the disclosed change in one or more dimensions, and the BII, using measured changes in radial and/or longitudinal dimensions (e.g., radius, length, curvature) of the pressed balloon relative to the same balloon when inflated free of constraints. A balloon that is inflated in free space (i.e., inflated and unconstrained), such as in a blood pool of a chamber of the heart, has, by definition, a BII of 100%. A balloon inflated in a constrained space, such as inside a lumen (e.g., a pulmonary vein) has a reduced radius while its length increases. The changed dimensions of the balloon correspond to a smaller BII, as calculated below, and the smaller BII provides an indication of how well the circular ostium of the pulmonary vein is occluded.

In some embodiments the balloon is first inflated in a blood pool, and the processor measures the dimensions of the inflated balloon in free space for use as a reference (i.e., measures the dimensions of the inflated and unconstrained balloon). Then the balloon is inserted into the PV ostium, and the processor measures the dimensions of the constrained (e.g., pressed) balloon. The processor calculates the BII based on one or more measured changes in balloon dimensions.

Furthermore, the detection can be performed by (a) comparison of the known mechanical shape and dimensions of the fully inflated balloon, e.g., outside the body, vs. a real time visualization of the defoamed balloon before ablation, and/or (b) monitoring in real time rapid changes in the balloon shape and dimensions that can occur due to force an external force exerted on the balloon by the physician pushing the inflated balloon against the PV ostium to fully occlude the PV.

In other embodiments, a deflated, or partially inflated, balloon is first inserted into the lumen and only then the balloon is inflated to occlude the lumen. In such a case, the processor calculates the BII using known dimensions of the free space inflated balloon as compared with one or more measured dimensions of the pressed balloon.

As indicated above, a BII may be defined by various changes in dimensions of the balloon. For example, assuming the balloon has a radius $R_0$ and length $L_0$ when freely inflated and, as a result of the balloon being inflated inside an ostium, the balloon radius drops by 10% (i.e., $\Delta R = -0.1 R_0$), and while, at the same time, the balloon elongates by 10% (i.e., $\Delta L = 0.1 L_0$), an inflation index defined as $$BII1 = 100 \cdot \frac{1 + \Delta R/R_0}{1 + \Delta L/L_0},$$

drops from 100% to 82%. Such a BII type is defined by a change in shape of the balloon from spherical to prolate spheroid.

In some embodiments, the processor measures the change in radius using position signals received from electrodes, e.g., ablation electrodes) disposed over a membrane of the balloon. The processor measures the change in length using additional position signals received from one or more sensors disposed proximally and/or distally to the balloon on a shaft to which the balloon is coupled.

In other embodiments, for example if the position signals are available only from one or more electrodes disposed over the membrane of the balloon, such as from ablation electrodes, the processor can calculate only a change in the radius of the balloon with reasonable accuracy, for example, of an equatorial radius of the balloon. In such a case, a BII may be defined in a way that depends only on the radius. For example, using a respective change in balloon curvature k, $k = 1/R$, $\Delta k = -\Delta R/R^2$, a radius-dependent BII2 is defined as $$BII2 = 100 \cdot \left(1 - \frac{\Delta k}{k}\right)^2,$$

where BII2 would drop from 100% to 81% when the balloon radius is reduced by 10%.

Based on the above comparison between BII1 or BII2 theoretical values, it may be sufficient to determine a degree of balloon occlusion solely using position signals from electrodes disposed over a membrane of the balloon. In practice, however, the accuracy of the measured positions of the balloon electrodes may be improved by using additional position signals, as described below. Therefore, the actual accuracy of BII1 may exceed that of BII2.

In an embodiment, the processor provides to a physician an indication of a degree of lumen occlusion in the form of a numerical grade comprising, for example, a BII value. In another embodiment, the processor outputs a textual indication that is based on the BII value, such as "Very Good" for a BII value between, for example, 75% and 84%, or "Insufficient" for a BII value between 95% and 100%, and so forth.

Typically, the processor is programmed in software containing a particular algorithm that enables the processor to conduct each of the processor-related steps and functions outlined above.

By providing an indication of a degree to which the ablation balloon occludes a lumen, for example through the disclosed BII value, the disclosed technique can improve accuracy of the balloon catheter positioning against lumen tissue and thereby improve effectiveness of balloon ablation. Furthermore, the disclosed technique, which does not require X-ray fluoroscopy imaging with use of contrast material, is safe for both patients and physicians.

The disclosed technique thus provides, in real time, a complete and safe assessment of individual balloon electrode contact with tissue, which may improve the outcome of cardiac balloon ablation treatments, such as of pulmonary vein (PV) isolation, as a treatment of arrhythmia.

System Description

Figure 1:
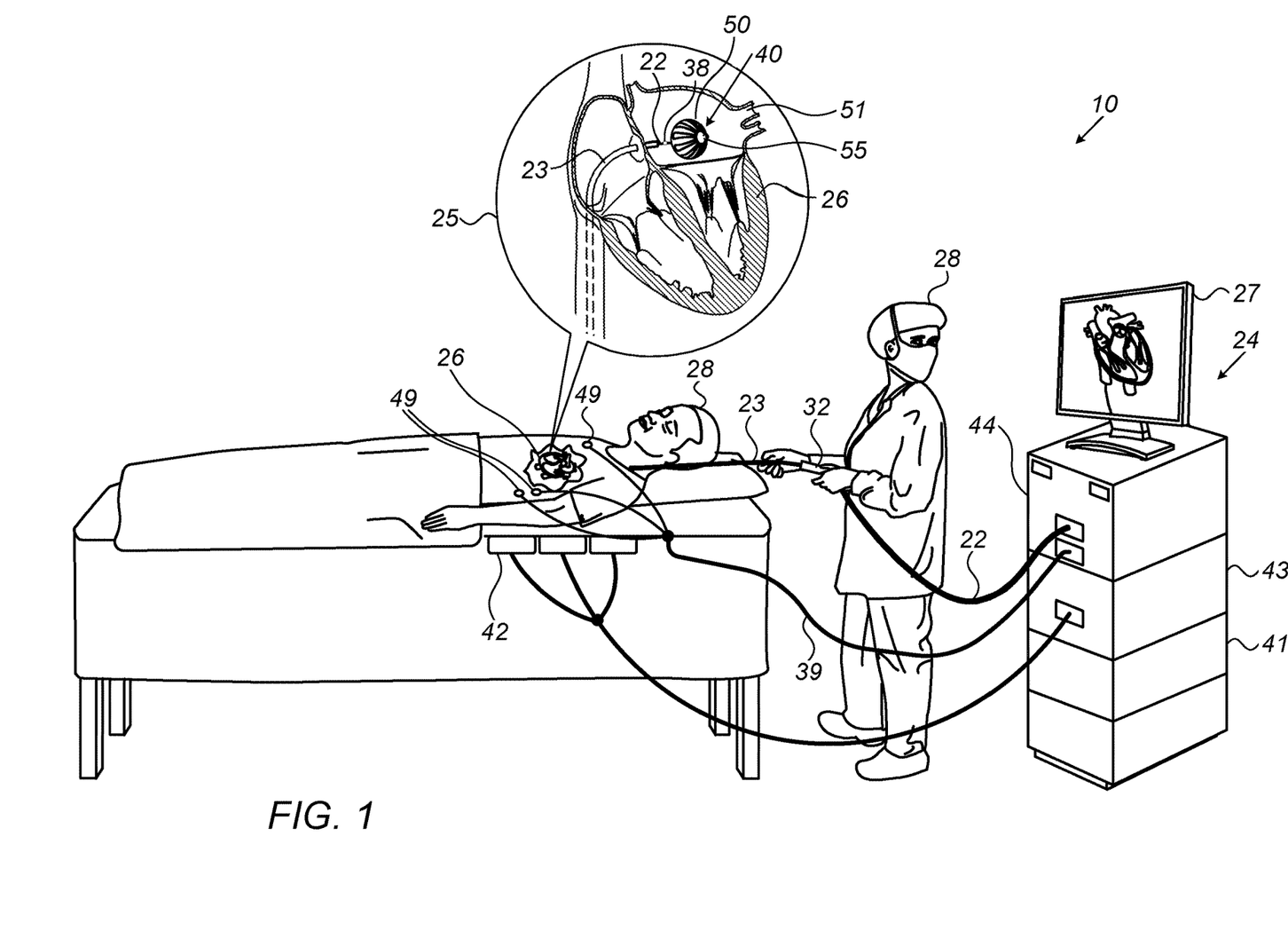
FIG. 1 is a schematic, pictorial illustration of a catheter-based position-tracking and ablation system comprising a radiofrequency (RF) ablation balloon, in accordance with an embodiment of the present invention.

FIG. 1 is a schematic, pictorial illustration of a catheter-based position-tracking and ablation system 20 comprising a radiofrequency (RF) ablation balloon 40, in accordance with an embodiment of the present invention. System 20 includes an Active Current Location (ACL) position tracking sub-system and, optionally, a magnetic position tracking sub-system. In some embodiments, system 20 is used for RF ablation of an ostium 51 of a PV (shown in inset 25) with balloon 40. The ACL sub-system is used to estimate a degree of inflation of balloon 40 after the balloon is inflated inside a lumen (e.g., an ostium), so as to ensure efficient subsequent balloon ablation.

Physician 30 navigates balloon 40 to a target lumen in a heart 26 of a patient 28 by manipulating a shaft 22 using a manipulator 32 near the proximal end of the catheter and/or deflection from a sheath 23. Balloon 40 is inserted, in a folded configuration, through sheath 23, and only after the balloon is retracted from sheath 23 does balloon catheter 40 regain its intended functional shape. By containing balloon catheter 40 in a folded configuration, sheath 23 also serves to minimize vascular trauma on its way to the target location.

To determine a degree of inflation of balloon 40, system 20 measures changes in one or more dimensions (e.g., radius and length) of balloon 40. To measure a change in dimension, a processor 41 of system 20 uses, at minimum, position signals from RF ablation electrodes 50 (seen in inset 25) of balloon 40, which function, for this purpose, as ACL sensing-electrodes.

Electrodes 50 are connected by wires running through shaft 22 to interface circuits 44 in a console 24 for receiving ACL signals. The ACL signals are measured relative to ACL surface electrodes 49, which are seen in the exemplified ACL system as attached by wires running through a cable 39 to the chest and to the back of patient 28. Console 24 drives a display 27, which shows the position and, optionally, the shape of balloon 40 inside heart 26.

The method of electrode position sensing using system 20 with ACL is implemented in various medical applications, for example in the CARTO™ system, produced by Biosense-Webster Inc. (Irvine, California) and is described in detail in U.S. Pat. Nos. 7,756,576, 7,869,865, 7,848,787, and 8,456,182, whose disclosures are all incorporated herein by reference with a copy provided in the Appendix of parent application Ser. No. 16/593,246.

As noted above, a BII value may be derived using only position-indicative signals from electrodes 50. However, to improve accuracy, signals from additional position sensors, such as sensors disposed on shaft 22 in the vicinity of balloon 40, may also be used. A method to improve accuracy of position measurement using additional signals received from position sensors disposed on the distal end of the shaft, such as from electrodes fitted on the shaft of the catheter on either side of the balloon, is described in U.S. Patent Application Publication No. 20190350489 A1 which is assigned to the assignee of the present patent application and whose disclosure is incorporated herein by reference.

Additionally or alternatively, additional position signals from a magnetic position sensor fitted in the distal end of shaft 22 may be used. In some embodiments, console 24 further comprises a magnetic position-sensing sub-system. Patient 28 is placed in a magnetic field generated by a pad containing magnetic field generator coils 42, which are driven by unit 43. The magnetic fields generated by coils 42 generate direction signals in a magnetic sensor 38, which are then provided as corresponding electrical inputs to processor 41, which uses these to calculate a direction of the distal end of shaft 22 to which balloon 40 is fitted, thus correcting the positions derived using the ACL method.

The method of position sensing using external magnetic fields is implemented in various medical applications, for example, in the CARTO™ system, produced by Biosense Webster Inc., and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference with a copy provided in the Appendix of parent application Ser. No. 16/593,246.

As indicated above, in some embodiments, the balloon catheter further comprises a distal position sensor 55, that can be a magnetic sensor or a sensing electrode used by the ACL sub-system. Using additional position signals from sensor 55 in combination with signals from magnetic sensor 38 and/or electrodes 50, processor 41 can estimate a change in length of the balloon catheter by estimating a change in a longitudinal distance (i.e., parallel to the distal end of shaft 22) between positions measured by the various sensors.

Processor 41 is typically a general-purpose computer programmed in software to carry out the functions described herein. In particular, processor 41 runs a dedicated algorithm as disclosed herein, including that shown in FIG. 3, that enables processor 41 to perform the disclosed steps, as further described below. The software may be downloaded to the computer in electronic form, over a network, for example, or it may, alternatively or additionally, be provided and/or stored on non-transitory tangible media, such as magnetic, optical, or electronic memory.

FIG. 1 shows only elements related to the disclosed techniques, for the sake of simplicity and clarity. System 20 typically comprises additional modules and elements that are not directly related to the disclosed techniques, and thus are intentionally omitted from FIG. 1 and from the corresponding description.

Figure 2A:
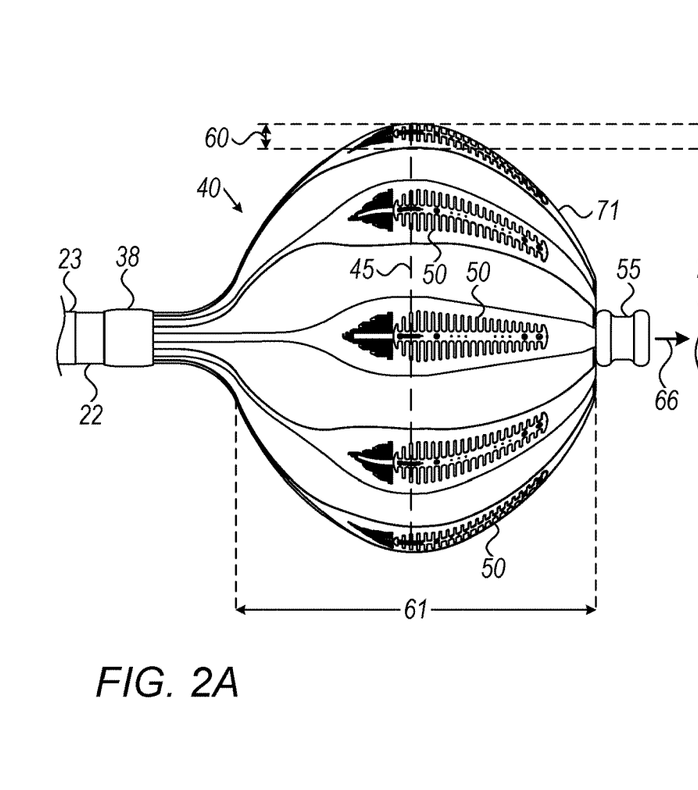
FIGS. 2A and 2B are schematic side-view illustrations of the balloon of FIG. 1 in free and constrained inflated states, respectively, in accordance with an embodiment of the present invention.
Figure 2B:
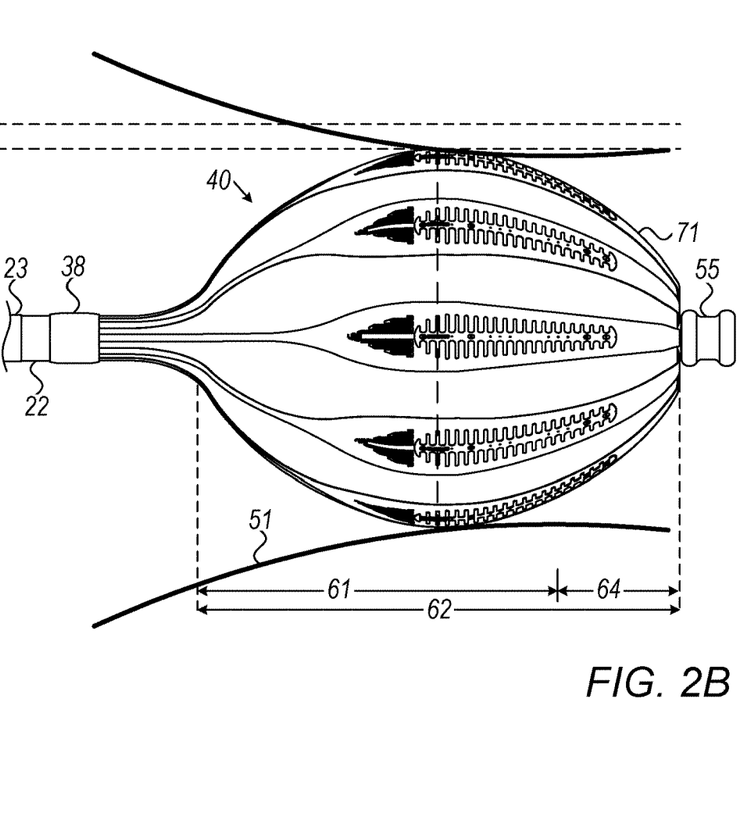

Identifying Pulmonary Vein Occlusion by Dimension Deformations of Balloon Catheter FIGS. 2A and 2B are schematic side-view illustrations of balloon 40 of FIG. 1 in free and constrained inflated states, respectively, in accordance with an embodiment of the present invention.

As seen in FIG. 2A, a balloon 40 inflated in free space resembles a sphere having an equator 45 about a longitudinal 66 axis that is parallel to the distal end of shaft 22. A length 61 is defined between a distal edge of the balloon, and a proximal end of the balloon.

Ablation electrodes 50 are seen disposed over a membrane 71 the balloon. Also seen are magnetic sensor 38 located just proximally to balloon 40 and a sensing-electrode 55, located just distally to the balloon. In some embodiments, a magnetic sensor replaces or is added to sensing-electrode 55.

FIG. 2B shown balloon 40 inflated to occlude ostium 51. As seen, due to the balloon being pressed against the walls of the ostium, the radius of the equator is reduced by a change 60 in the radius. Furthermore, the balloon is characterized by an increased length 62 along longitudinal axis 66 of the balloon, as the shape of the balloon comes to resemble a prolate spheroid.

Using the measured change (e.g., a decrease 60) in radius ΔR of an equator 45, and the measured change (e.g., an increase 64) in length, ΔL, from length 61 to length 62, processor 22 can derive a BII value using, for example, $$BII1 = 100 \cdot \frac{1 + \Delta R/R_0}{1 + \Delta L/L_0}.$$

where ΔR is the change in radius of the balloon; $R_0$ is the original radius of the unconstrained balloon; ΔL is the change in length of the balloon; and $L_0$ is the original length of the unconstrained balloon.

The illustration shown in FIG. 2 is chosen purely for the sake of conceptual clarity. Other geometries of ablation electrodes are possible. Elements which are not relevant to the disclosed embodiments of the invention, such as irrigation ports and temperature sensors, are omitted for the sake of clarity.

Figure 3:
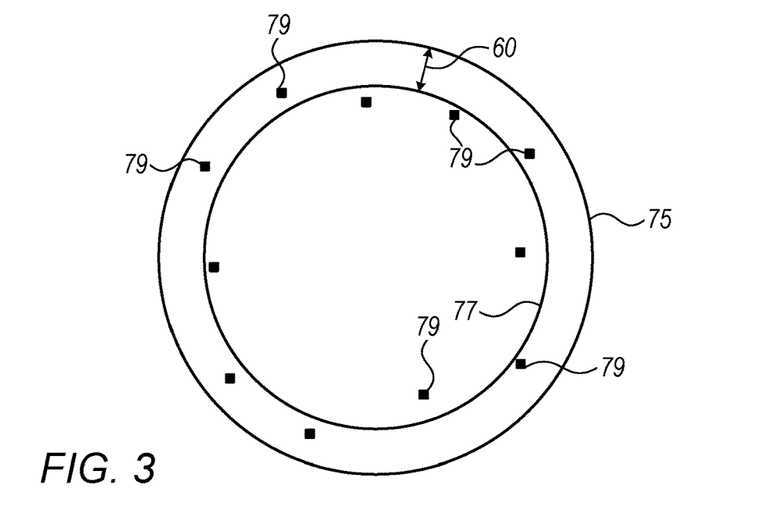
FIG. 3 is a plot that schematically illustrates a derivation of a change in the radius of the balloon of FIGS. 2A and 2B using Active Current Location (ACL) measurements, in accordance with an embodiment of the present invention.

FIG. 3 is a plot that schematically illustrates a derivation of a change in a radius of the balloon of FIGS. 2A and 2B using Active Current Location (ACL) measurements, in accordance with an embodiment of the present invention. Circle 75 represents equator 45 of the balloon inflated in free space, where equator 45 has a known radius, typically in the range of ten to fifteen millimeters, depending on the balloon model.

Radial positions 79 (FIG. 3) of electrode 50 are derived by processor 41 using ACL signals from ablation electrodes 50 and surface electrodes 49 (i.e., using the aforementioned ACL method). Using, for example, calibration, radial positions 79 represent approximately a circle on a plane defined by equator 45. To find a radial change 60, processor 41 fits a circle 77 to radial positions 79 and calculates radial change 60 as the difference between the known radius of circle 75 and the radius of fitted circle 77.

Processor 41 then calculates a BII, for example, using $$BII2 = 100 \cdot \left(1 - \frac{\Delta k}{k}\right)^2,$$

where k, defined by k=1/R, is the respective curvature of the balloon, Δk, $\Delta k = -\Delta R/R^2$ is a respective change in balloon curvature calculated from radial change 60, ΔR, and using an average of radiuses 75 and 77, R.

BII2, which is derived solely using signals from ablation electrodes disposed over a membrane of balloon 40, may be sufficiently accurate to estimate a degree of occlusion. However, using additional position signals, such as from sensors 38 and/or 55 disposed on shaft 22 proximally and distally to balloon 40, respectively, may improve the accuracy of measured positions 79 and therefore the accuracy of BII2.

Figure 4:
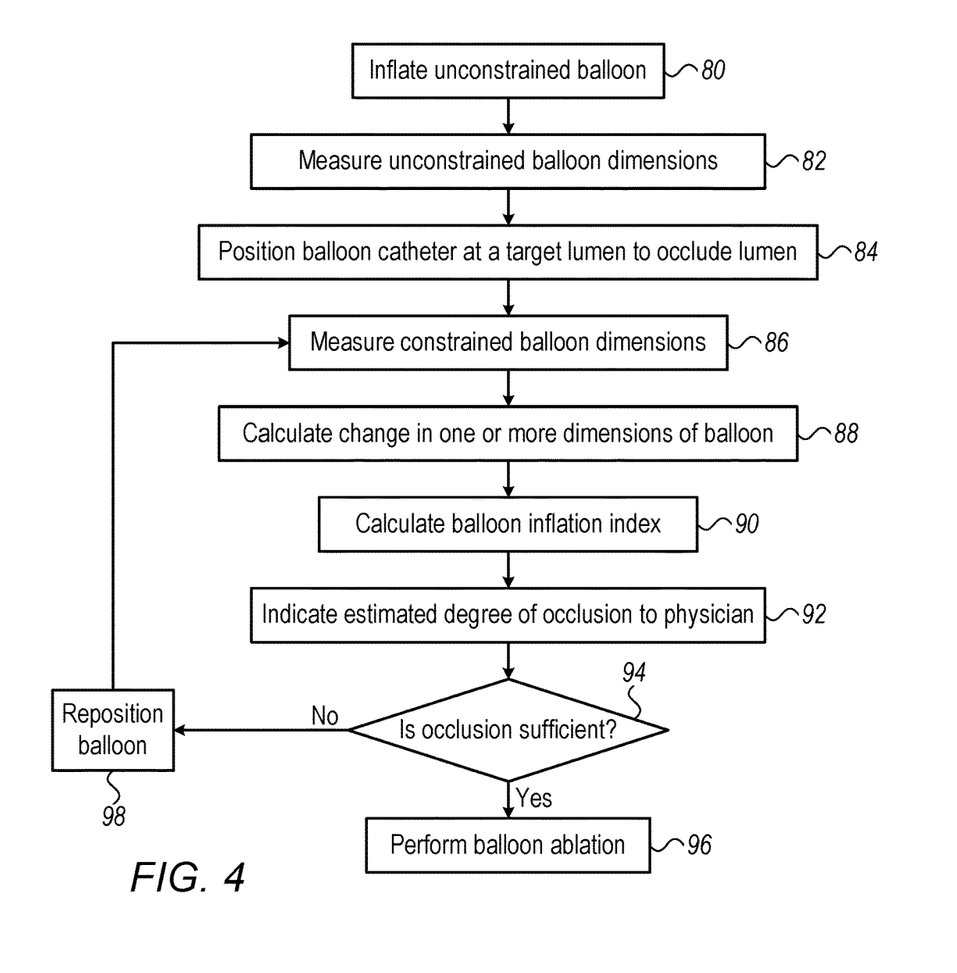
FIG. 4 is a flow chart that schematically illustrates a method and algorithm for estimating a degree of occlusion of an ostium by the balloon of FIG. 1, in accordance with an embodiment of the present invention.

FIG. 4 is a flow chart that schematically illustrates a method and algorithm for estimating a degree of occlusion of an ostium by balloon 40 of FIG. 1, in accordance with an embodiment of the present invention. The algorithm, according to the present embodiment, carries out a process that begins with physician 30 inflating the balloon unconstrained, e.g., in the blood pool within the heart, at a balloon inflation step 80. Next, at a first balloon measuring step 82, system 20 uses electrodes 50 and surface electrode 49 via ACL, magnetic or a hybrid ACL and magnetic location sensing technique to determine, i.e., to measure the unconstrained balloon dimensions, such as to determine a radius of the unconstrained balloon 40, e.g., of an equator 45 of unconstrained balloon 40.

Next, physician 30 positions balloon catheter 40 at a target location inside a lumen of heart 26, such as at an ostium of a pulmonary vein, at a balloon positioning step 84. At a constrained balloon measuring step 86, system 20 uses electrodes 50 and electrode 55 to measure a radius of pressed balloon 40, e.g., of an equator 45 of pressed balloon 40. Next, based on the measured equatorial radius of the freely inflated balloon 40, and, that of the pressed balloon, processor 41 calculates the change 60 in balloon equatorial radius, at a balloon dimensions change calculation step 88.

In an embodiment, processor 41 applies in step 88 the method described in FIG. 3 to derive radial change 60 (i.e., reduction in radius).

Next, using calculated change 60, processor 41 calculates a balloon inflation index (BII), such as BII2, at BII calculation step 90.

Based on the calculated balloon inflation index, system 20 indicates to physician 30 a degree of occlusion of the ostium, for example, by presenting a grade on display 27, at an occlusion indicating step 92.

Based on the grade, physician 30 decides if balloon 40 is positioned sufficiently well, relative to the ostium, at a decision step 94.

If physician 30 decides that balloon 40 occludes the ostium sufficiently well, then physician 30 performs a treatment, such as an RF ablation, in an RF balloon treatment step 96.

If, on the other hand, the physician 30 decides that balloon 40 does not occlude the ostium sufficiently, the process goes to a repositioning step 98, during which physician 30 attempts to better occlude the ostium. The process then loops to step 86 to remeasure constrained balloon constrained balloon dimensions and to re-estimate the degree of occlusion.

The example flow chart shown in FIG. 4 is chosen purely for the sake of conceptual clarity. The present embodiment also comprises additional steps of the algorithm, such as acquiring X-ray images, which have been omitted from the disclosure herein purposely on order to provide a more simplified flow chart. In addition, other steps, such as applying irrigation, are omitted for clarity of presentation.

Although the embodiments described herein mainly address cardiac applications, the methods and systems described herein can also be used in other applications, such as in otolaryngology, neurology, cardiology, blood vessel treatment and renal denervation.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   receiving position signals that are indicative of positions of multiple electrodes disposed on an expandable end effector that is fitted at a distal end of a shaft configured to engage a lumen of an organ;
   based on the received position signals, calculating a change in one or more dimensions of the expandable end effector between (i) a first configuration in which the expandable end effector is expanded but not engaged in the lumen, and (ii) a second configuration in which the expandable end effector is expanded and engaged in the lumen;
   using the calculated change, deriving an index indicative of an estimated degree to which the expandable end effector is expanded in the lumen, the index being based at least in part on a respective change in a curvature of the expandable end effector between the first configuration and the second configuration; and
   presenting the estimated degree to which the expandable end effector is expanded in the lumen.

2. The method according to claim 1, wherein the index is derived by the following equation:
   $index = 100(1-(\Delta k/k))_2$ where $k$ is a respective curvature of the expandable end effector and $\Delta k$ is the respective change in the curvature of the expandable end effector between the first configuration and the second configuration.

3. The method according to claim 1, wherein calculating the change in the one or more dimensions comprises calculating a change in a radius of the expandable end effector.

4. The method according to claim 3, wherein calculating the change in the radius of the expandable end effector comprises:
   measuring positions of ablation electrodes disposed over the expandable end effector using Active Current Location (ACL);
   best fitting a circle to the measured positions; and
   calculating a radius of the best fitted circle.

5. The method according to claim 1, wherein receiving the position signals comprises receiving additional position signals from one or more position sensors disposed on the distal end of the shaft, and wherein calculating the change in the one or more dimensions comprises calculating a change in a length of the expandable end effector along a longitudinal axis of the expandable end effector based on the additional position signals.

6. The method according to claim 5, wherein the index is further derived by the following equation:
   $index = 100[(1+(\Delta R/R_0))/(1-(\Delta L/L_0))]$ where $\Delta R$ is a change in radius of the expandable end effector, $R_0$ is a radius of the expandable end effector in the first configuration, $\Delta L$ is the change in the length of the expandable end effector, and $L_0$ is a length of the expandable end effector in the first configuration.

7. The method according to claim 5, wherein the one or more position sensors are magnetic sensors.

8. The method according to claim 1, wherein estimating the degree to which the expandable end effector is expanded in the lumen comprises numerically grading the degree.

9. The method according to claim 1, wherein estimating the degree to which the expandable end effector is expanded in the lumen comprises textually grading the degree.

10. The method according to claim 1, wherein the lumen comprises an ostium of a pulmonary vein (PV).

11. A system, comprising:
    an interface, configured to receive position signals that are indicative of positions of multiple electrodes disposed on an expandable end effector that is fitted at a distal end of a shaft configured to engage a lumen of an organ; and
    a processor, which is configured to:
      based on the received position signals, calculate a change in one or more dimensions of the expandable end effector;
      using the calculated change in dimensions, derive an index indicative of an estimated degree to which the expandable end effector is expanded in the lumen, the index being based at least in part on a respective change in expandable end effector curvature between (i) a first configuration in which the expandable end effector is expanded but not engaged in the lumen, and (ii) a second configuration in which the expandable end effector is expanded and engaged in the lumen; and
      present the estimated degree to which the expandable end effector is expanded in the lumen.

12. The system according to claim 11, wherein the index is derived by the following equation:
    $index = 100(1-(\Delta k/k))^2$ where $k$ is a respective curvature of the expandable end effector and $\Delta k$ is the respective change in the curvature of the expandable end effector between the first configuration and the second configuration.

13. The system according to claim 11, wherein the processor is configured to calculate the change in the one or more dimensions by calculating a change in a radius of the expandable end effector.

14. The system according to claim 13, wherein the processor is configured to calculate the change in the radius of the expandable end effector by:
    receiving measured positions of ablation electrodes disposed over the expandable end effector using Active Current Location (ACL);
    best fitting a circle to the measured positions; and
    calculating a radius of the best fitted circle.

15. The system according to claim 11, wherein the processor is configured to receive additional position signals from one or more position sensors disposed on the distal end of the shaft, and to calculate the change in the one or more dimensions by calculating a change in a length of the expandable end effector along a longitudinal axis of the expandable end effector based on the additional position signals.

16. The system according to claim 15, wherein the index is further derived by the following equation:
    $index = 100[(1+(\Delta R/R_0))/(1-(\Delta L/L_0))]$ where $\Delta R$ is a change in radius of the expandable end effector, $R_0$ is a radius of the expandable end effector in the first configuration, $\Delta L$ is the change in the length of the expandable end effector, and $L_0$ is a length of the expandable end effector in the first configuration.

17. The system according to claim 15, wherein the one or more position sensors are magnetic sensors.

18. The system according to claim 11, wherein the processor is configured to estimate the degree to which the expandable end effector is expanded in the lumen by numerically grading the degree.

19. The system according to claim 11, wherein the processor is configured to estimate the degree to which the expandable end effector is expanded in the lumen by textually grading the degree.

20. The system according to claim 11, wherein the lumen comprises an ostium of a pulmonary vein (PV).

* * * * *